United States Patent [19]

Clarke, Jr.

[11] Patent Number: 4,876,091
[45] Date of Patent: Oct. 24, 1989

[54] GYPSUM-BASED INSECTICIDE PELLETS AND METHOD OF MANUFACTURE

[76] Inventor: John L. Clarke, Jr., 402 Fairbank Rd., Riverside, Ill. 60546

[21] Appl. No.: 273,206

[22] Filed: Nov. 18, 1988

Related U.S. Application Data

[63] Continuation-in-part of Ser. No. 125,150, Nov. 25, 1987, which is a continuation-in-part of Ser. No. 904,905, Sep. 8, 1986, abandoned.

[51] Int. Cl.$^4$ .................... A01N 25/00; A01N 63/00; A01M 1/20
[52] U.S. Cl. .................... 424/421; 424/484; 424/489; 428/330; 428/404; 428/703
[58] Field of Search .............. 424/421, 409, 484, 489; 428/703, 404, 330, 331

[56] References Cited

U.S. PATENT DOCUMENTS

| | | |
|---|---|---|
| 879,877 | 2/1908 | Kennedy . |
| 2,023,459 | 12/1935 | Bachman .................... 424/421 X |
| 2,974,030 | 3/1961 | Geary . |
| 3,034,882 | 5/1962 | Renwick . |
| 3,161,497 | 12/1964 | Amburn . |
| 3,172,752 | 3/1965 | Pierce . |
| 3,252,785 | 5/1966 | Hoblit . |
| 3,274,052 | 9/1966 | Yaffe et al. .................... 424/421 |
| 3,316,901 | 5/1967 | Smith . |
| 3,502,458 | 2/1967 | Schenk . |
| 3,664,963 | 5/1972 | Pasin . |
| 3,780,195 | 12/1973 | Balassa . |
| 3,904,662 | 9/1975 | Henrick et al. . |
| 3,912,815 | 10/1975 | Henrick et al. . |
| 3,941,772 | 3/1976 | Ploger et al. . |
| 3,953,191 | 4/1976 | Barton . |
| 3,953,378 | 4/1976 | Lasser . |
| 4,034,086 | 7/1977 | Ploger et al. . |
| 4,053,112 | 10/1977 | Vander Hooven et al. . |
| 4,166,112 | 8/1979 | Goldberg . |
| 4,221,599 | 9/1980 | Deleuil . |
| 4,222,984 | 9/1980 | Ladwig . |
| 4,225,361 | 9/1980 | Joseph . |
| 4,247,403 | 1/1981 | Foley et al. . |
| 4,260,422 | 4/1981 | Thamm et al. . |
| 4,271,118 | 6/1981 | Schreiner-Hansen . |
| 4,401,473 | 8/1983 | Kleiner et al. . |
| 4,464,317 | 8/1984 | Thies et al. .................... 424/421 X |
| 4,563,344 | 1/1986 | Kotz et al. . |
| 4,670,039 | 6/1987 | Sjogren . |
| 4,732,762 | 3/1988 | Sjogren . |

FOREIGN PATENT DOCUMENTS

| | | |
|---|---|---|
| 702663 | 1/1965 | Canada . |
| 816050 | 6/1969 | Canada . |
| 1129668 | 8/1982 | Canada . |

OTHER PUBLICATIONS

"Field Evaluations of Dursban Insecticide Briquettes When Used as Mosquito Larvicide Materials," Mosquito News, Dec. 1970, vol. 30, No. 4, pp. 563–566.
"Control of Southern House Mosquito Larvae in Louisiana Papermill Log Ponds," Journal of Economic Entomology, Oct. 1969, vol. 62, No. 5, pp. 1152–1154.
"Cold Fog ULV Insecticide Applications Using the Leco Model HD Fog Generator and Dursban Blocks in Catch Basins," presented by Edward Dornlas, Benton County, Oregon, Health Dept., 1972.

*Primary Examiner*—Nancy A. B. Swisher
*Attorney, Agent, or Firm*—Kinzer, Plyer, Dorn, McEachran & Jambor

[57] ABSTRACT

A machine distributable gypsum-based pesticide pellet in which the gypsum is a solid formed by the bonding of plaster of paris and water which includes, prior to formation of the solid, by weight, no more than the minimum water required for substantial hydration of the plaster of paris. The pellet includes approximately five percent of a pesticide with the balance being plaster of paris. The pesticide, water and plaster of paris are generally uniformly mixed to provide a pellet which has a generally uniform release of the pesticide over its life. The pellet after setting has essentially no free water in that substantially all water is absorbed in the chemical reaction between the plaster of paris and water. The pellet has a maximum surface area of about 180 mm$^2$, a maximum weight of about 0.3 gram, and has been compressed in the extrusion process to eliminate porosity and external and internal voids.

10 Claims, No Drawings

GYPSUM-BASED INSECTICIDE PELLETS AND METHOD OF MANUFACTURE

SUMMARY OF THE INVENTION

This application is a continuation-in-part of copending application Ser. No. 125,150, filed Nov.25, 1987, which is a continuation-in-part of co-pending application Serial No. 904,905, filed Sept. 8, 1986 now abandoned.

Mosquitoes breed in the presence of water when physical and meteorological conditions are favorable. Most species develop in the presence of very little water; a few inches are all that is necessary to stimulate egg hatch. Small shallow sites are often more productive per unit area than large zones. In natural sites, eggs are often laid on soils along the sloping, vegetated margins of shallow depressions. These eggs may survive many dry seasons and then hatch when heavy rains or flooding activates the sites. A marsh may flood in its entirety, then as the sheet of water covering the marsh recedes or evaporates, the newly-hatched larvae are left to develop in small isolated ponds, i.e. between cattail roots and canary grass pockets. These pools or pockets remain isolated as the mosquito larvae develop, pupate, and emerge as adults within three to 14 days after the flooding rain. The pools and pool margins then dry and additional eggs are conditioned for the next flooding.

In order to effectively control mosquito breeding in the highly productive isolated pools, it is necessary to have an effective long-lasting, yet environmentally safe, dosage rate of insecticide in place in each pocket before flooding occurs. The present state of the art relies on 8.3 gram plaster/insecticide briquets which are placed by hand throughout the marsh on ten foot centers at 30 day intervals. When the marsh floods, the briquets begin dissolving and some toxicant is carried by the continuous sheet of water throughout the marsh; however, as the water recedes, the mosquito larvae are isolated in small shallow pockets, 12 to 24 inches in diameter. As a result, only in the pocket which has the large briquet will mosquito larvae be controlled. With the large briquets, too much insecticide is concentrated in too small an area with potentially adverse effects on desirable wildlife. The adjacent pools, isolated from the large briquet, continue to produce mosquitoes. The great need is to distribute product in a slow release form to each isolated pocket throughout the marsh without using additional large briquets, and drastically increasing the amount of toxicant and the cost of treatment per acre.

The present invention is specifically directed to a slow release insecticide pellet, having a weight of approximately 0.3 gram or less which, when applied at the customary rate of 8 lbs. per acre will provide a pellet for each two square feet of marsh surface area.

Another purpose of the invention is to fabricate a plaster insecticide pellet, utilizing common inexpensive molding plaster having approximately 2,000 psi compressive strength which will provide consistent control of mosquitoes over 30 to 60 days of immersion in water.

Another purpose is a mosquito control pellet of a size and shape that can be accurately metered and dispersed by ground and helicopter application equipment.

Another purpose is to provide a slow release insecticide pellet in which the pellet, prior to setting, contains no more than the minimum of water required to chemically convert plaster of paris to gypsum with reduced internal and external voids and with reduced porosity to thus reduce the surface area available to the dissolving medium.

Another purpose is a controlled release insecticide pellet.

Another purpose is a pellet of the type described which has a uniform release rate over its life.

Other purposes will appear in the ensuing specification and claims.

DESCRIPTION OF THE PREFERRED EMBODIMENT

The present invention relates to a gypsum-based pesticide and in particular to such a product which is useful in destroying mosquito larvae. Although the invention will be described in connection with pesticides particularly known for killing mosquito larvae, the product may, with the use of different pesticides or herbicides, be useful in destroying other types of pests and both terrestrial and aquatic weeds. The invention may also be useful as a carrier for insect repellents.

The principal factor in determining the release time of pesticides which are in solid form is the size of the product, its porosity, solubility, and the manner in which the pesticide is embodied into its carrier. The larger products, for example briquets of the 50 gram size, of necessity must be placed in a mosquito breeding area by hand. Whereas, smaller products, for example in the 0.3 to 0.15 gram category or less, may be applied by helicopter, substantially reducing the time and cost in seeding a mosquito breeding area. However, prior products which were of a size to be distributed by helicopter did not utilize a carrier which would provide a long release time.

For example, in the past the insecticide temephos, known by the trademark ABATE, manufactured by American Cyanamid, has been sprayed on sand or clay particles and then this material has been spread by machine over a mosquito breeding area. Such products have a life of 24 to 48 hours, which requires not only more timely application, but subsequent applications to completely destroy mosquito larvae.

To manufacture the conventionally used 8.3 gram molded briquets, a dry powder compound of 28.2 lbs. of carbon impregnated with toxicant is dry blended with 71.8 lbs of molding plaster. The dry blend is placed in a Hobart mixer and blended with 51.5 lbs. of deionized water. The resulting slurry is then poured into plastic trays having 400 molds each in the form of a truncated cone with approximate dimensions of 24 mm in major diameter, 19 mm in minor diameter, and 19 mm in height. After the plaster mixture is added to the molds, each mold is evened out with a squeegee to ensure even distribution to each pocket, then vibrated to release trapped air. The plaster hardens within one to two hours, then is cured at 120° F. for 24 hours to remove excess free water not used to react plaster of paris to gypsum. Of the 151.5 lbs. of total weight initially blended, only 112.9 lbs. or 75 percent of molded product remained after drying. The resulting cast briquets are extremely porous and because of the porosity have a specific gravity of just 1.21 grams/cm$^3$. The surface area of each briquet is 20.33 cm$^2$. The surface area per acre for 8 lbs. or 435 briquets is 8,844 cm$^2$.

The present invention provides a method of manufacturing a gypsum-based pesticide pellet which permits products as small as 0.15 gram and no heavier than 0.3 gram. The pesticide is uniformly mixed providing uniform release rate. The pellets are not porous and have almost no surface or internal voids, ensuring a release rate dependent on surface area. Two known pesticides which are satisfactory are methoprene and temephos manufactured by Zoecon and American Cyanamid, respectively.

Considering specifically a product using the pesticide methoprene, the pesticide in an amount, by weight, of approximately 4.5 to 5 percent is mixed with no greater than 20 percent water, with the balance being plaster of paris. More specifically, the methoprene may be included in the mixture in the form of a methoprene premix which consists of carbon and methoprene. The carbon not only functions to some degree as a carrier for the methoprene, but principally functions as a sun block to prevent biodegradation of the methoprene. The composition as described is intimately or uniformly mixed in a mixing device known as a turbolizer, for example of the type used in the mixing of foundry sands and manufactured by Material Processing Corp. of Elmhurst, Ill. Such a device has a chamber in which the water, pesticide and plaster of paris are introduced and within the chamber is a series of rotating blades which rotate at an extremely high speed and will intimately mix the described mixture in no more than three to five seconds.

The mixture described, after going through the turbolizer, is transferred to a pellet mill of the type manufactured by CPM Corporation of San Francisco, Calif., which extrudes pellets at approximately 1,000 psi which both densifies the product and eliminates any ingrained voids. Preferably, the pellet mill will provide a product having an average weight of 0.15 gram and a minimum specific gravity of on the order of about 1.70 grams.cm/$^3$.

The mixture described has a short setting time, for example ten minutes, because the amount of water used is the minimum required to completely set the plaster of paris into gypsum. The amount of water required is 18.6 percent of the weight of the plaster of paris and thus, normally the maximum water used in the process described herein will be no more than 20 percent. With such an amount of water the setting time is short, but since only a fraction of the setting time has been used in the mixing stage, no more than five seconds, there is adequate time for the mixture to pass through a pellet mill.

The product coming from the pellet mill, which will have the composition described, will then be applied to a tumbling or vibrating screen in which undersized products are screened out and in which the webbing normally attendant to product formation will be knocked off the pellets. The screening step not only sizes the product, but permits the product to cool. Any fines from the screening process may be sent back to the mixing chamber for recycling before the plaster is completely set. However, the important point in terms of the screening process is not only to size the product, but to permit adequate cooling. Recycling is economically important in making the maximum use of the ingredients and is possible because of the short mixing and forming cycle.

In addition to methoprene-based pesticide pellets, the pesticide temephos similarly may be used. A mixture consisting of about five percent temephos, no more than 20 percent water, with the balance plaster of paris, can also be utilized in the described process. A temephos insecticide as commercially available is in the form of an emulsifiable concentrate. In the case of temephos, it is not necessary to have a sun blocking ingredient in this particular formulation.

The use of gypsum as a carrier for a pesticide is particularly advantageous in that it has a pH of 7, meaning that it is neutral and thus, not being either an acid or a base, will have no chemical effect on the pesticide.

Of particular importance in the invention is the use of no more water than the minimum required to set the mixture. This insures a product which can be economically manufactured in that there is no requirement for a long drying period for the product to reach a solid state and to reach its minimum final dried weight. Since a minimum amount of water very substantially reduces the setting time of plaster of paris, it is necessary to provide a method of uniformly mixing a pesticide, water and plaster of paris in a very short period of time, preferably only a fraction of the setting time. This is done by the rotating turbolizer described herein. The mixing is complete in a period of time which provides adequate remaining time for final formation of the product.

The pellets formed by the above-described process contain no more than the minimum amount of water necessary to convert the plaster of paris to gypsum, with the result that no free water is left in the pellet. Thus, there is no evaporation and no porosity develops during curing. It has been determined that if free water is present in the product after formation, the product must either be dried with heated air or allowed to dry over time at room temperature, both drying processes having undesirable side effects. If the product is dried with high temperature air, concentration of the pesticide is degraded. If the product is allowed to dry at room temperature over time, mildew and mold form on the product, preventing complete release of the pesticide. In the present invention, no drying step is needed, as the pellets cure to full strength in about one hour.

Pellets formed by the above-described process have a substantially higher specific gravity than those of the prior art, particularly those shown in U.S. Pat. No. 4,732,762. The specific gravity of the pellets formed as described herein is approximately 1.70 grams.cm$^3$ vs. approximately 1.21 grams cm$^3$ for a product of the type shown in the '762 patent.

The surface area of pellets formed as disclosed herein and using the customary application of 8 lbs. of pellets per acre results in 30,809 cm$^2$ of area available to release pesticide. In contrast, the surface area of briquets formed in accordance with the '762 patent is only 8,845 cm$^2$. The smaller pellets provide 3.44 times the surface area for the same weight of product. Thus, the pellets disclosed herein provide both a constant release rate and a longer release period and uniformly distribute the pesticide over the target area.

Because the pellets formed in accordance with the process disclosed herein have a substantially greater specific gravity than prior art briquets and have little, if any, porosity, even with the greater surface area the pellets will dissolve and thus release insecticide at a substantially slower rate than briquets of the prior art having much less surface area and much greater size. The lack of porosity and the increased specific gravity is substantially important in providing a pellet which will have a uniform release rate over a substantial period of time The smallest pellet which may be formed by the above-described process and which can be machine distributed is a cylinder having a diameter of 1.6 mm, a length of 3.2 mm, and a surface area of 17.7 mm$^2$. The largest pellet which can be produced by the described process and which can be machine distributed has a diameter of 4.8mm, a length of 9.6 mm and a surface area of 177.4 mm$^2$. A preferred size is a pellet having a diameter of 4 mm, a length of 8 mm, and a surface area of 125.7 mm$^2$. Such preferred pellets have a weight of on the order of about 0.15 gram and an average specific gravity of 1.70 grams.cm/$^3$.

Tests comparing pellets made in accordance with the present invention with those of the prior art, particularly those shown in the '762 patent, indicate that the prior art briquets, having substantial porosity, initially absorb water and therefore gain weight with the porosity causing the product to dissolve from both the exterior surface and the interior voids, resulting in an initial release of a substantially greater amount of pesticide and a resulting release of a smaller amount of pesticide after several days of immersion in water. In contrast, pellets formed in accordance with the present invention dissolve at a uniform rate and tests have shown that release of the pesticide is generally uniform over the life of the product. This is particularly due to the fact that the pellet is concentrated —has a higher density than pellets of the prior art —and has no surface voids and very little porosity and thus release of the uniformly mixed pesticide is from the surface of the pellet.

Whereas the preferred form of the invention has been shown and described herein, it should be realized that there may be many modifications, substitutions and alteration thereto.

The embodiments of the invention in which an exclusive property or privilege is claimed are defined as follows:

1. A machine distributable gypsum-based pesticide product which is non-porous and substantially without internal or external voids and in which the gypsum is a solid formed by the bonding of plaster of paris and water which includes, prior to formation of the solid, by weight, no more than the minimum water required for substantial hydration of the plaster of paris, approximately 5 percent of a pesticide, with the balance plaster of paris, the pesticide, water and plaster of paris being generally uniformly mixed to provide for generally uniform release of the pesticide over the life of the product, the product, after setting, having essentially no free water in that substantially all water is absorbed in the chemical reaction between the plaster of Paris and water, the product having a maximum surface area of on the order of about 180 mm$^2$, and a maximum weight of on the order of about 0.3 gram.

2. The product of claim 1 further characterized in that said product is generally cylindrical in shape and has a maximum diameter of on the order of about 4.75 mm.

3. The product of claim 1 further characterized in that said product is generally cylindrical in shape and has a maximum length of on the order of about 9.5 mm.

4. The product of claim 1 further characterized in that said product has a minimum specific gravity of on the order of about 1.70 grams,/cm$^3$.

5. The product of claim 1 further characterized in that said product has a diameter of on the order of about 4 mm, a length of on the order of about 8 mm, and a surface area of on the order of about 125 mm$^2$.

6. The product of claim 1 further characterized by and including a sun blocking material to prevent degradation of the pesticide.

7. The product of claim 1 further characterized in that the pesticide is methoprene.

8. The product of claim 7 further characterized in that the pesticide methoprene is introduced into the mixture prior to bonding as a premix of carbon and methoprene.

9. The product of claim 1 further characterized in that the pesticide is temephos.

10. The product of claim 1 further characterized in that said product has a minimum surface area of on the order of about 17.7 mm$^2$.

* * * * *